United States Patent [19]
Gipson et al.

[11] Patent Number: 4,964,860
[45] Date of Patent: Oct. 23, 1990

[54] DETACHABLE TWO PIECE ABSORBENT GARMENT

[75] Inventors: William P. Gipson; Michael W. Mason, both of Cincinnati; Thomas A. Hensler, West Chester, all of Ohio

[73] Assignee: The Procter & Gamble Company, Cincinnati, Ohio

[21] Appl. No.: 382,157

[22] Filed: Jul. 18, 1990

[51] Int. Cl.⁵ ............................................. A61F 13/15
[52] U.S. Cl. ..................................... 604/391; 604/392
[58] Field of Search ............... 604/391, 392, 393, 394, 604/396, 398

[56] References Cited

U.S. PATENT DOCUMENTS

| | | | |
|---|---|---|---|
| 849,725 | 4/1907 | Cook | 604/398 |
| 3,335,721 | 8/1967 | Gastwirth | 604/391 |
| 3,452,753 | 7/1969 | Sanford | 604/401 |
| 3,618,608 | 11/1971 | Brink | 604/391 |
| 4,051,854 | 10/1977 | Aaron | 604/394 |
| 4,158,906 | 6/1979 | Watson | 24/83 |
| 4,315,508 | 2/1982 | Bolick | 604/391 |
| 4,505,707 | 3/1985 | Feeney | 604/392 |
| 4,537,591 | 8/1985 | Coates | 604/391 |
| 4,617,022 | 10/1986 | Pigneul | 604/391 |
| 4,819,846 | 4/1989 | Hannemann | 224/240 |

FOREIGN PATENT DOCUMENTS

2612770 9/1988 France .

Primary Examiner—Randall L. Green
Assistant Examiner—Gary Jackson
Attorney, Agent, or Firm—Larry L. Huston; John M. Pollaro; Fredrick H. Braun

[57] ABSTRACT

A two piece garment for collecting bodily discharges is disclosed. The garment has a belt and a disposable assembly which are detachable and reattachable. The belt is intended to be reused, while the disposable assembly is intended to be discarded when soiled. The two components are attached to one another by hook and loop type fastening material, providing for adjustment to fit a wide range of wearer sizes.

18 Claims, 3 Drawing Sheets

DETACHABLE TWO PIECE ABSORBENT GARMENT

FIELD OF THE INVENTION

This invention is directed to absorbent garments worn to assist in the collection of bodily discharges and, more particularly, to garments which have detachable components which may either be reused or discarded, as desired.

BACKGROUND OF THE INVENTION

Garments and related articles which protect against incontinence are well known in the art. These garments typically have a body portion which holds or otherwise positions an absorbent core against the body of the wearer and an attachment means which retains the garment in position as the wearer moves. For example, U.S. Pat. No. 4,315,508, issued Feb. 16, 1982, to Bolick discloses a garment suspension system including two elastic strips. The suspension strips are disposed on either side of the garment and provide self-centering and a vertical vector force for maintaining the garment in place. U.S. Pat. Nos. 3,618,608, issued Nov. 9, 1971, to Brink and 4,051,854 issued Oct. 4, 1977, to Aaron disclose diapers having integral belts secured with hook and loop type fasteners. France Pat. No. 2,612,770 published Sept. 30, 1988, in the name of Motte discloses disposable pants having integral straps which encircle the waist of the wearer and are secured by fasteners. The pants are drawn between the legs of the wearer and fastened to the outside of the integral straps.

The prior art does not, however, teach an absorbent garment having detachable components which may either be durable and reusable or, alternatively, disposed of if soiled and not suitable for reuse. Accordingly, it is an object of this invention to provide a garment for the collection of bodily discharges and capable of having clean and reusable components detached and laundered or restored as necessary. Further, it is an object of this invention to provide a garment having detachable components which may be disposed of if unsanitary or otherwise not suitable for reuse. Finally, it is an object of this invention to provide a garment in which not all components need to be repurchased by the consumer every time the garment is worn and soiled.

BRIEF SUMMARY OF THE INVENTION

This invention comprises a detachable two piece garment having a reusable belt and a disposable assembly. The reusable belt has receiving material substantially along its length and at least one patch of complementary hook type material disposed near an end of the belt. The hook type material is adapted to be refastenably attached to the receiving material of the belt. The disposable assembly comprises a liquid pervious topsheet, a liquid impervious backsheet at least partially peripherally joined to the topsheet, and an absorbent core intermediate the topsheet and the backsheet. The disposable assembly further has liquid impervious flaps overlaying the topsheet and defining four corners. A patch of complementary hook type material may be disposed on the flaps near each corner of the disposable assembly and adapted to be refastenably attached to the receiving material of the belt.

BRIEF DESCRIPTION OF THE DRAWINGS

While the Specification concludes with claims particularly pointing out and distinctly claiming the present invention, it is believed the invention will be better understood from the following description taken in conjunction with the accompanying drawings, wherein like parts are given the same reference numeral and:

DETAILED DESCRIPTION OF THE INVENTION

Figure 1:
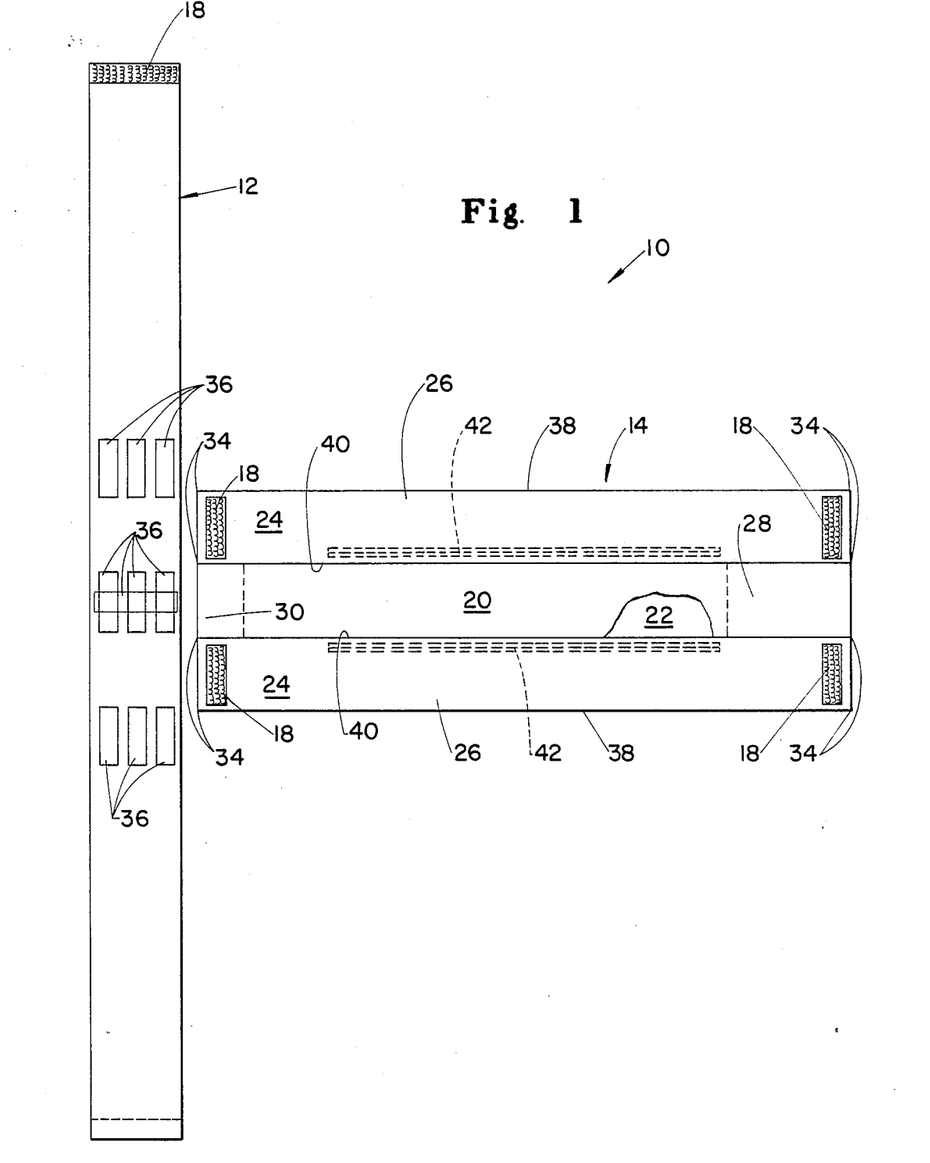
FIG. 1 is a top plan view of an embodiment of the present invention having no elastic induced contraction and showing the belt and disposable assembly detached.

As shown in FIG. 1, the invention comprises a detachable two piece absorbent garment 10, suitable for use as an incontinence aid. The garment 10 features a reusable belt 12 and a disposable assembly 14. The reusable belt 12 is made of receiving material, suitable for refastenably attaching to complementary hook style mechanical fasteners. The belt 12 has a fastening means, preferably patches 18 of the hook type material disposed on either end for securing the belt 12 about the waist of a wearer. As used herein, components of a garment 10 are considered "detachable" which may be attached and removed more than one time, without destruction or undue distortion of either component.

Figure 2:
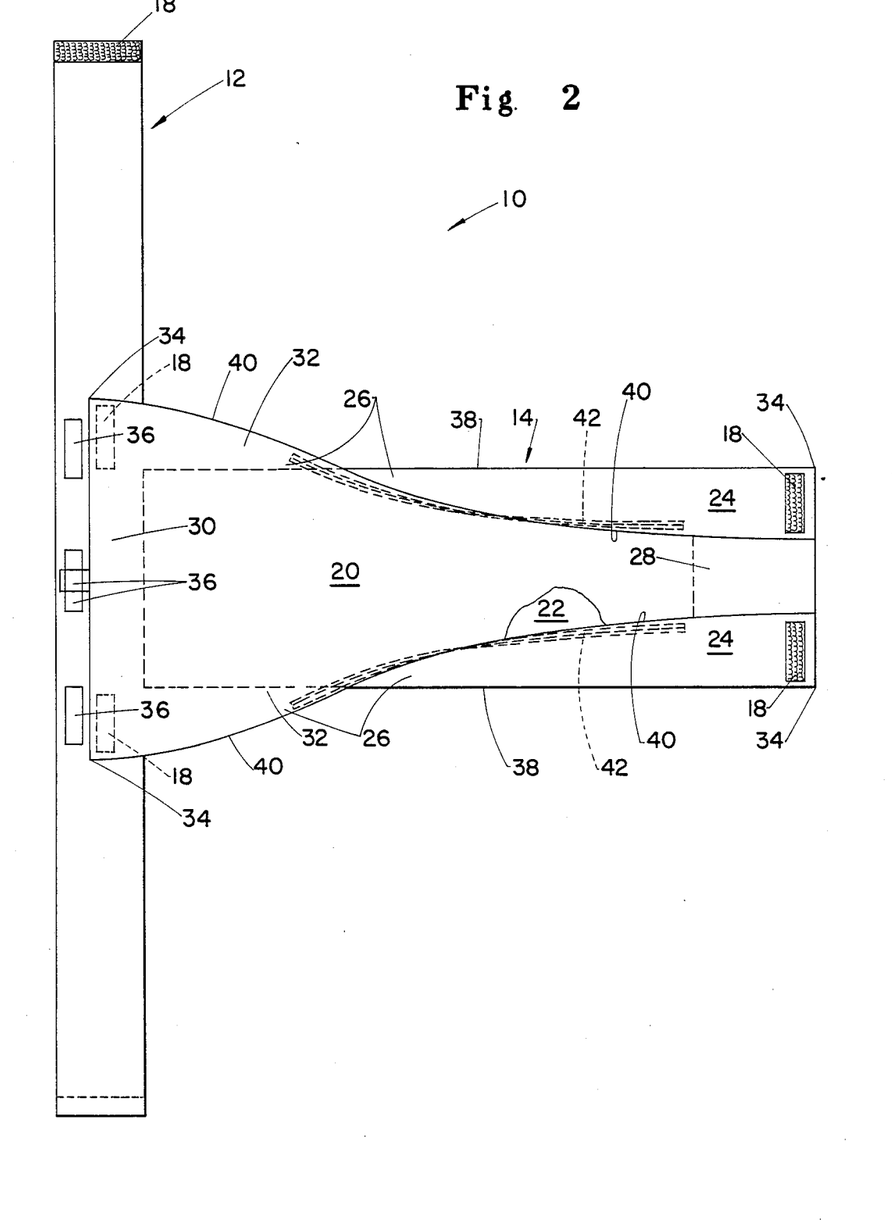
FIG. 2 is a top plan view showing the inflected flaps of the disposable assembly attached to the belt.

The disposable assembly 14 has a liquid pervious topsheet 20 which overlays an absorbent core 22 which, in turn, overlays a liquid impervious backsheet 24. The backsheet 24 and topsheet 20 have longitudinal side margins 32, as shown in FIG. 2, which are folded over the core 22 and topsheet 20, forming flaps 26 and providing a somewhat C-shaped cross section. The flaps 26 may be elasticized to seal the disposable assembly 14 more closely to the legs of the wearer. The disposable assembly 14 may be generally rectangularly shaped having front and rear waist margins 28 and 30 connected by longitudinal side margins 32, as seen in the top plan view, and which defines four corners 34 of the flaps 26. A patch 18 of hook type mechanical fastening material is disposed at each corner 34 of the flaps 26 and faces away from the core 22.

The garment 10 herein described is laid out in the flat, uncontracted configuration of FIG. 1 unless otherwise specified. Examining each component of the garment 10 in more detail, one notes that the disposable assembly 14 is substantially symmetrically disposed about the longitudinal centerline of the garment 10.

As used herein, the term "garment" refers to an article worn about the lower torso, typically by an incontinent person, for the collection of bodily discharges. The term "longitudinal" refers to an imaginary line, axis, or direction of the garment 10, which line, axis or direction extends between the transverse edges of the garment 10 and is generally aligned with the vertical plane which bisects a standing wearer into left and right body halves. The term "lateral" refers to an imaginary line, axis or direction generally orthogonal the longitudinal direction and is generally sideways aligned relative the wearer. The garment 10 described herein is sized to a wearer having a measurement ranging from about 81 centimeters to about 112 centimeters around the hips. It is to be understood by one skilled in the art that the garment 10 described herein is to be appropriately scaled for a different size of wearer.

The "belt" is the component of the garment 10 to which both waist margins 28 and 30 of the disposable assembly 14 are attached, which encircles the waist of the wearer, and holds the disposable assembly 14 against the wearer. The belt 12 is, as shown, generally rectangular in shape and has a length of about 112 centimeters to accommodate the aforementioned range of wearer sizes. The belt 12 preferably has a width of at least about 6.5 centimeters to about 13 centimeters, preferably about 9 centimeters, to provide for variations in longitudinal positioning of the disposable assembly 14. If the belt 12 is narrower or wider it may not provide adequate adjustment to fit the wearer or may interfere with the leg movements of the wearer, respectively.

The belt 12 is preferably reusable, and is not intended to be soiled by the collection of bodily discharges or disposed of when the core 22 becomes loaded by such bodily discharges. As used herein, the term "reusable" refers to a garment 10, or component thereof, intended to be laundered and reused rather than to be discarded after a single use. The belt 12 should be clean in appearance, nonirritating to the skin of the wearer, and able to accommodate a wide range of wearer sizes. Although not required, it may be desirable to have one belt 12 matched to a given wearer over a period of time or, alternatively, a belt 12 interchanged among various wearers.

The belt 12 has receiving material, disposed at various positions along the length, to provide for attachment of the belt 12 about the waist of the wearer and of the disposable assembly 14 to the belt 12. Preferably, the loop style receiving material is disposed on both faces of the belt 12, along the entire length of the belt 12, to provide for more versatility in attachment of the disposable assembly 14. As used herein, the term "receiving material" refers to material having an exposed surface with tightly spaced openings complementary to hook type material, discussed below, and which openings are defined by one or more strands or fibers, or; alternatively, is capable of localized elastic deformations, so that the complementary hook type material may become entrapped and not withdrawn without interference. For the embodiment described herein, loop material having a pile depth of about 0.8 millimeters works well.

The belt 12 may be of a single or double thickness, depending upon whether the receiving material has one or two exposed faces complementary to the hook type material. The openings or localized elastic deformations allow for entry of the hook type material into the exposed surface of the receiving material, while the fibers, strands or nondeformed areas of the receiving material prevent, withdrawal or release of the hook type material until either it is so desired by the user or the peel or shear strength is exceeded. Loop style receiving material sold by Guilford Mills, Incorporated of New York, N.Y. as Model Number 19029 has been found to work well.

Preferably, a patch 18 of complementary hook type material is disposed near each end of the belt 12, to provide for securing of the belt 12 about the waist of the wearer. As used herein, the term "hook type material" refers to any material having a fastening system joined to and projecting from a substrate. The fastening system may have one or more mechanical engaging means which project, typically radially, from a shank which is joined to the substrate or may be adhesive. The engaging means is typically the portion of the hook type material which penetrates and is secured to the exposed surface of the complementary receiving material. Suitable hook type material is sold by the Minnesota Mining and Manufacturing Company of Minneapolis, Minn. as Model Number XPO-0040. Hook type material and receiving material are considered "complementary" if the openings between the strands or fibers are sized to allow at least one engaging means of the hook type material to penetrate into the exposed surface of the receiving material and to be engaged or intercepted thereby.

The hook type material described herein, preferably has a peel strength of at least about 300 grams but which does not exceed about 1,000 grams to provide for adequate attachment of the components discussed herein, but which is not so great as to provide undue resistance when it is desired to remove the garment 10 or inspect it for the accumulation of bodily discharges. A peel strength of about 500 grams is generally preferred. The patch 18 should have a minimum shear strength of about 1,000 grams. A patch 18 of hook type material at each end of the belt 12 about 1.9 centimeters wide and coterminous with the longer edges of the belt 12 is suitable.

The edges of the belt 12 may be sewn or reinforced with a material, such as rib knit material, to prevent the belt 12 from becoming frayed or the exposed surfaces of receiving material from separating (if the belt 12 is made of a double thickness). The sewing, or other reinforcement, should be generally smooth, nonirritating to the skin of the wearer, and not provide an undue increase in the thickness of the belt 12, otherwise the wearer may experience discomfort. If desired, the longer edges of the belt 12 may be curvilinear and arcuate in the same direction, so that the top edge of the belt 12 is of a lesser radius of curvature and more closely conforms to the wearer.

The belt 12 may be provided with indicia 36, such as targets or visual markings, so that the longitudinal centerline of the belt 12 becomes apparent and may be matched to the longitudinal centerline of the disposable assembly 14. The indicia 36 may be sized to the shape of the hook type patches 18 disposed on the corners 34 of the flaps 26, to indicate to the user an appropriate location for attaching such patches 18 to the belt 12. The indicia 36 may be longitudinally spaced, to assist in adjustment of the belt 12, relative to the disposable assembly 14, in the longitudinal direction. The indicia 36 may be sewn, printed on or applied to the belt 12 in any permanent manner.

The indicia 36 allow the user to repeatedly attach the disposable assembly 14 to the belt 12 on an ephemeral basis, so that readjustment and refitting (particularly in the longitudinal direction) is minimized. It will be apparent to one skilled in the art, that the herein described belt 12, even with indicia 36, lo allows for an infinite adjustment of the disposable assembly 14 relative to the receiving material of the belt 12. For example, if a wearer's size does not correspond to the placement of the indicia 36, the disposable assembly 14 may be attached to the belt 12 at any position intermediate the indicia 36. Indicia 36 which allows adjustment in accordance with the teachings of U.S. Pat. No. 4,662,875 issued May 5, 1987 to Hirotsu et al., and incorporated herein by reference for the purpose of showing a preferred type of indicia 36 and materials, are suitable.

The disposable assembly 14 may be of any shape suitable for holding an absorbent core 22 about the anus and genitalia of the wearer. The term "disposable assembly" refers to the combination of a backsheet 24, absorbent core 22, topsheet 20, and one or more flaps 26 typically, but not necessarily, longitudinally coextensive of the disposable assembly 14. The term "disposable" or component thereof, intended to be discarded after a single use and not to be laundered or otherwise restored and reused.

The disposable assembly 14 may be of a quadrilateral shape, preferably rectangular, so that each side is substantially symmetric about the longitudinal centerline and a mirror image of the other side. Preferably, the disposable assembly 14 has a greater longitudinal dimension than lateral dimension, to provide full coverage from the front waist margin 28 to the rear waist margin 30 around the lower abdominal region and torso of the wearer. For the embodiment described herein, a generally rectangular disposable assembly 14 having a longitudinal dimension of about 64 centimeters to about 79 centimeters preferably about 71 centimeters, and a lateral dimension of about 38 centimeters has been found suitable.

The disposable assembly 14 comprises a liquid pervious topsheet 20, a liquid impervious backsheet 24 and an absorbent core 22 intermediate the topsheet 20 and backsheet 24. The topsheet 20 and backsheet 24 are at least partially peripherally joined in face to face relation, circumscribing the periphery of the core 22 and capturing it in the desired position and orientation. Preferably, the topsheet 20 and backsheet 24 are joined throughout any portions which extend beyond, i.e., are outboard of, the periphery of the core 22. More preferably, the topsheet 20 and backsheet 24 are generally coextensive.

The disposable assembly 14 should be soft, flexible and provide comfort to the wearer. The term "flexible" refers to the condition of materials which are generally compliant and readily conform to the shape and contours of the human body. Preferably, the disposable assembly 14 is not noisy, to provide discretion for the wearer. Generally, the disposable assembly 14 should have minimal elongation in the longitudinal direction, so the garment 10 will be tight fitting in the crotch region and firmly position the absorbent core 22 against the body.

The disposable assembly 14 has two waist margins, a front waist margin 28 and a rear waist margin 30. The front waist margin 28 and rear waist margin 30 are to the front and rear of the wearer, respectively, as the garment 10 is worn. The term "waist margin" refers to either of the two portions of the garment 10 which includes and is intermediate the lateral edge of the garment 10 and the corresponding lateral edge of the core 22 and is generally at the highest elevation of the garment 10 while it is worn. Edges are "corresponding" if they are the closer of the two edges of like kind and disposed on the same side of the longitudinal or lateral centerline. If desired, the waist margins may be laterally extensible.

The disposable assembly 14 also has two longitudinal side margins 32, one disposed to either side of the longitudinal centerline and towards the wearer's left and right sides. The term "longitudinal side margin" refers to that portion of the garment 10 intermediate the longitudinal edge of the garment 10 and the corresponding longitudinal edge of the core 22. The longitudinal side margins 32 form the flaps 26 of the garment 10 as described in more detail below. Preferably, the longitudinal side margins 32 and waist margins are formed from the coextensive portions of the topsheet 20 and backsheet 24 joined in face to face relation, which portions are respectively laterally and longitudinally outboard of the core 22.

To provide flaps 26 of a suitable geometry, the backsheet 24 and topsheet 20 are coextensive and wider, i.e., greater in lateral dimension, than the core 22. Each flap 26 should laterally extend about 5 to about 8 centimeters from the corresponding longitudinal edge of the core 22, so that the flap 26 can stand away from the core 22 and provide for containment of bodily discharges, particularly in the crotch region of the garment 10.

The core 22 is centered on and between the topsheet 20 and backsheet 24, so that each longitudinal side margin 32 may be folded about the longitudinal edge of the core 22, forming a flap 26. The term "flap" refers to the component of the garment 10, specifically of the disposable assembly 14, which overlays the core 22 and the outwardly facing surface of the topsheet 20. The proximal edge 38 of the flap 26 is coincident with the fold line and is the longitudinal edge of the topsheet 20 and backsheet 24 at the peripheral seal adjacent the longitudinal edge of the core 22. When the flaps 26 are folded about this fold line, the distal edge 40 of the flap 26 will overlay the longitudinal edge of the core 22 about 7 centimeters, providing a minimum distance of about 3.3 centimeters between the distal edge 40 of the flap 26 and the longitudinal centerline.

This arrangement creates a urine target zone in the exposed area of the topsheet 20 between the flaps 26. The urine target zone is intermediate the flaps 26 and extends from about 5 centimeters to about 25 centimeters from the front lateral edge of the core 22 towards the rear waist margin 30. Also the longitudinal dimension of the front waist margin 28 should not be too great, otherwise, a pocket too small for the male wearer may result. The target zone should be somewhat less than described above if the inflected flap 26 arrangement is not used.

As illustrated, when the flaps 26 overlay the topsheet 20 and core 22, the distal edges 40 of the flaps 26 are preferably generally parallel. The distal edges 40 ends of the flaps 26 and the longitudinal edges of the disposable assembly 14 intersect to define four corners 34, each corner 34 having a patch 18 of hook type material complementary to the receiving material of the belt 12.

Disposed on at least one and preferably each of the four corners 34 and facing away from the topsheet 20, is an outwardly facing patch 18 of the hook type material, complementary to the receiving material of the belt 12. Thus, a pair of patches 18 of hook type material is disposed at both the front and rear waist margins 28 and 30, with each patch 18 facing in the same general outward direction (away from the core 22). The patches 18 should preferably be juxtaposed with the corners 34 and may laterally extend substantially the entire lateral dimension of the flaps 26.

Each patch 18 may be spaced inwardly from the lateral and longitudinal edges of the flaps 26 at least approximately 0.6 centimeters, to provide for variations in positioning during manufacture and obviate the rough edge of the patch 18 from contacting and irritating the skin of the wearer. The patches 18 may be polygonol, preferably rectangular in shape. Such shape preferably has a greater lateral dimension than longitudinal dimension, with the longitudinal dimension being less than the width of the belt 12, to provide for longitudinal adjustment of the disposable assembly 14 relative to the belt 12.

The patches 18 may be joined to the flaps 26 using any means well known in the art, which means exceeds the desired peel and shear strengths. Hot melt adhesive bonding, as discussed above, using Minnesota Mining and Manufacturing Company model number XPO-9-035 adhesive has been found suitable. Patches 18 made of Minnesota Mining and Manufacturing Company Model No. XPO-0040 hook type material, described above, are particularly suitable and complementary to the receiving material of the belt 12 described herein.

The distal edges 40 of the flaps 26 may monotonically taper towards the lateral centerline as either waist margin 28 or 30, particularly the front waist margin 28, is approached. Alternatively the distal edges 40 of the flaps 26 may be arcuate, particularly concave towards the longitudinal centerline, so that a wider access to the topsheet 20 is provided as the lateral centerline of the garment 10 is approached.

The distal edges 40 of the flaps 26 may be reinforced, entirely or in part, with elastic 42 to form a barrier leg cuff which more securely seals the flaps 26 against the inner thigh of the wearer and provides a mechanism for the flaps 26 to be spaced from the core 22 and topsheet 20. The elastic 42 need not extend into the rear waist margin 30 of the garment 10. Further, the elastic 42 should not be disposed too close to any of the patches 18 of hook type material, particularly those patches 18 disposed near the front waist margin 28 of the garment 10, otherwise bunching and wrinkling of the garment 10 near the patches 18 may occur and the target zone for urine may be reduced, possibly allowing leakage, particularly for a male wearer.

Preferably, the elastic 42 is somewhat centered on the distal edge 40 of the flap 26. The elastic 42 is preferably extended about 75 to about 95 percent, more preferably about 85 percent as the flaps 26 conform to the shape of the wearer. For the embodiment described herein, having a longitudinal dimension at the distal edges 40 of the flaps 26 of about 71 centimeters, the elastic 42 may terminate at least about 3 to about 15 centimeters from the front waist margin 28 and about 3 to 25 centimeters from the rear waist margin 30.

The elastic 42 should provide a high degree of extensibility, o without undue contractive force and should be under tension when joined to the garment 10. Elastic 42 which relaxes about 20 percent of its extended length when an applied load of about 400 grams is reduced to an applied load of about 100 grams force is adequate.

The elastic 42 may be either a single strand of elastomeric material, or parallel multiple strands of elastic material, as desired. If a single strand of elastic 42 is selected, a rubber strand made by Fulflex Inc. of Middletown, R.I. and sold as Model No. 9411 has been found suitable. The single strand of elastic 42 may be adhered to the flap 26 with 691-336-20 adhesive sold by the Findley Adhesives Company of Wauwatosa, Wis. This elastic 42 may be prestretched about 180 percent before being joined to the flap 26.

If multiple strands of elastic 42 are selected, 940 Decitex Lycra sold by the DuPont Corporation of Wilmington, Del. and intermittently adhered to the flap 26 with a spiral adhesive pattern using the Findley H2031 works well. A particularly suitable execution has four parallel strands of the Lycra elastic 42, each prestretched about 250–450 percent, preferably about 300 percent, when joined to the flaps 26.

The elastic 42 is preferably joined to the flaps 26 intermediate the topsheet 20 and backsheet 24, so that the elastic 42 does not contact and irritate the skin of the wearer when the flaps 26 are folded about the longitudinal edges of the core. The elastic 42 may be attached to the flaps 26 using any method known in the art, such as that disclosed in U.S. Pat. No. 4,081,301, issued Mar. 28, 1978, to Buell, which patent is incorporated herein by reference for the purpose of showing a particularly preferred method of joining the elastic 42 to the flaps 26. Alternatively, the elastic 42 may be adhesively coated with an intermittent spiral pattern of adhesive.

The absorbent core 22 provides the means to collect and contain bodily discharges, particularly urine, deposited thereon. The term "core" refers to the component of the garment 10 which receives and retains the bodily discharges. The core 22 is disposable and should be conformable and nonirritating to the skin. Suitable core 22 materials include layers of tissue, such as cellulose wadding and fibrated communition pulp or airfelt, and absorbent gelling materials. The core 22 need not have a total absorbent capacity much greater than the total amount of bodily discharges to be absorbed and is preferably narrow and thin so as to be comfortable to the wearer. For the embodiment and wearer described herein, the capacity is preferably not less than about 350 grams of urine.

The core 22 should be sized to register with the disposable assembly 14 of the garment 10, and be laterally narrower than the topsheet 20 and backsheet 24. For the embodiment described herein, a generally quadrilaterally shaped core 22 having a greater longitudinal dimension than lateral dimension is suitable. Preferably, the core 22 is somewhat hourglass shaped, having notches to accommodate the legs, as shown. The core 22 may be about 56 centimeters in the longitudinal direction, about 15 centimeters in lateral dimension at the notches, and about 23 centimeters in lateral dimension at the inboard lateral edges of the waist margins. This geometry provides a margin between the lateral edges of the core 22 and the corresponding lateral edge of the disposable assembly 14 of about 7.5 centimeters in longitudinal dimension.

The core 22 is preferentially interposed between the topsheet 20 and the backsheet 24 to prevent the absorbent material of the core 22 from shredding and becoming detached while the garment 10 is worn and to insure containment of bodily discharges. This arrangement also provides for a unitary disposable assembly 14 which can be easily attached to and detached from the belt 12.

The core 22 is preferentially joined to the backsheet 24. The term "join" refers to the condition where a first member or component is affixed, or connected, to a second member or component either directly; or indirectly, where the first member or component is affixed, or connected, to an intermediate member or component which in turn is affixed, or connected, to the second member or component. The association between the first member, or component, and the second member, or component, is intended to remain for the life of the garment 10. Joining is preferentially accomplished by adhesive bonding the core 22 to the backsheet 24. The adhesive may be applied in any suitable spray pattern or longitudinally oriented beads. Adhesive sold under the tradename 990C by the Findley Adhesives Company of Wauwatosa, Wis., has been found to work well for this purpose.

The topsheet 20 is oriented towards and contacts the body of the wearer. The topsheet 20 is liquid pervious and should be flexible, clean in appearance, and somewhat opaque to hide bodily discharges collected in and absorbed by the core 22. The topsheet 20 should exhibit good strikethrough and rewet characteristics, permitting bodily discharges to rapidly penetrate the topsheet 20 to the core 22, but not flow back through the topsheet 20 to the skin of the wearer. A perforated polyolefinic film or nonwoven topsheet 20 having about 5 to about 60 percent open area, typically about 25% open area, and a thickness of about 0.01 to about 0.05 millimeters is suitable. Model P1522 film made by the Ethyl Corporation, Visqueen Division of Terre Haute, Ind. and James River Corporation of Richmond, Va. Model Number MSP-T090 Celestra IV-0.55 nonwoven material have been found to work well.

The backsheet 24 may be any flexible, liquid impervious film, such as a polyolefinic film and prevents discharges absorbed by the core 22 from soiling the clothing and bedding of the wearer. The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness preferably about 0.04 millimeters has been found to work well. Polyethylene films sold by the Ethyl Corporation, Visqueen Division as Model Number XP-3985 has been found particularly well-suited for this purpose.

Referring to FIG. 2, to apply the garment 10 to the wearer, a clean and sanitary disposable assembly 14 is provided and may be attached to either face of the belt 12, using the indicia 36, or positions intermediate the indicia 36, as desired. To facilitate such attachment, the flaps 26 may be inflected at the rear waist margin 30, so that the pair of patches 18 of hook type material at the rear waist margin 30 face opposite the pair of patches 18 at the front waist margin 28. The pair of rear waist margin 30 patches 18 are then attached to a first face of the belt 12. The wearer sits or stands, holding one end of the belt 12 in each hand with the disposable assembly 14 behind the wearer and downwardly oriented. The wearer encircles his or her waist with the belt 12, and secures the ends of the belt 12 to any intermediate portion of the belt 12 having receiving material by using the fastening means on each end of the belt 12.

Figure 3:
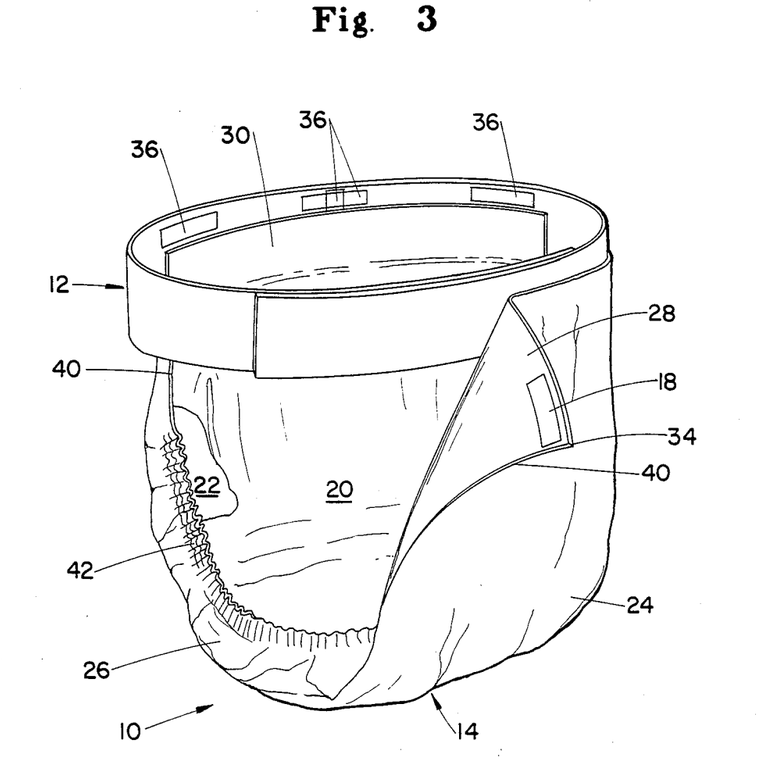
FIG. 3 is a perspective view of the embodiment of FIG. 1 partially secured about a wearer (not shown).

Referring to FIG. 3, the disposable assembly 14 is then brought between the legs of the wearer and secured in front of the wearer to the opposite or second face of the belt 12 using the remaining pair of hook type patches 18 at the front waist margin 28. Utilizing this arrangement, the pair of hook type patches 18 at the rear waist margin 30 of the disposable assembly 14 is attached to the face of the belt 12 which is inwardly oriented (towards the waist of the wearer) and the pair of hook type patches 18 at the front waist margin 28 is attached to the outwardly oriented face of the belt 12 (away from the wearer).

By attaching the front of the disposable assembly 14 to the exterior face of the belt 12, the garment 10 is easily inspected for soiling. If soiled, the disposable assembly 14 is detached from the belt 12 and replaced with a new disposable assembly 14. The belt 12 is reused, and laundered as necessary.

In a variant embodiment (not shown), the outwardly facing patches 18 are not disposed on the flaps 26, but rather are joined to the exposed and outwardly facing surface of the backsheet 24. The disposable assembly 14 of the garment 10 may be thought of as having a lateral centerline bisecting the garment 10 into a front portion and a rear portion, to the front and rear of the wearer, as the garment 10 is worn, respectively. The disposable assembly 14 may be further thought of as having four quadrants, defined by the longitudinal and lateral centerlines.

In such an embodiment one patch 18 is disposed in each quadrant of the backsheet 24 defined by the longitudinal and lateral centerlines. Preferably, each such patch 18 is juxtaposed with a corner of the disposable assembly 14. Utilizing this arrangement, the patches 18 are attached to the inwardly facing surface of the belt 12 at both the front waist margin 28 and the rear waist margin 30.

In another variant, a longitudinally oriented patch 18, disposed on the backsheet 24, at or near the longitudinal centerline, extends from the front portion of the garment 10 to the rear portion of the garment 10. Alternatively, two longitudinally oriented patches 18 may be provided on the backsheet 24, one patch 18 disposed on either side of the longitudinal centerline, each patch 18 preferably within the longitudinal marginal portions 32. Each longitudinally extending patch 18 extends into both the front and rear portions of the garment, preferably to the front and rear waist margins 28 and 30.

In a related variant, one longitudinally oriented outwardly facing patch 18, is disposed on each flap 26. The longitudinally oriented patch 18 extends from the front portion of the garment 10 to the rear portion of the garment 10, so that both the front and rear waist margins 28 and 30 may be secured to the belt 12.

In another variant (not shown) two laterally oriented patches 18 are joined to the backsheet 24. In such an embodiment, one patch 18, in the front portion and one patch 18 in the rear portion laterally extend to both sides of the longitudinal centerline, so that both the front and rear waist margins 28 and 30 may be attached to the belt 12. Additionally a patch 18 may be disposed on the backsheet 24 coincident with the longitudinal centerline.

It will be apparent to one skilled in the art that any of the aforementioned embodiments having an arrangement of patches 18 joined to the backsheet 24 will not have the inflected flaps 26 of FIG. 2 and may even omit such flaps 26.

Yet another variation is to substitute patches 18 of adhesive for the patches 18 of hook type material in any of the aforementioned executions. Suitable adhesive is sold by Eastman Chemical Products Company of Kingsport, Tenn. under the tradename Eastobond A-3. If adhesive patches 18 are selected, the belt 12 should be adapted to provide a complementary surface to which the patches 18 of the adhesive will readily adhere. A belt 12 having complementary zones corresponding to the positions of attachment of the patches 18 and made of polyethylene, in accordance with the aforementioned and incorporated U.S. Pat. No. 4,662,875 is suitable. Alternatively, the patches 18 of adhesive may be disposed on the belt 12 and the complementary zones disposed on the flaps 26 or backsheet 24 as described above.

It will be apparent that combinations of the foregoing embodiments are feasible and that other joining means (such as snaps or fasteners) may be substituted for the adhesive and hook type patches 18 discussed above. It will be further apparent to one skilled in the art that several other variations are feasible without departure from the spirit and scope of the claimed invention.

What is claimed is:

1. A garment having a front portion, a rear portion and a longitudinal centerline, said garment comprising:
   a belt having a first face and a second face opposed thereto, said belt comprising receiving material and at least one patch of complementary hook type material adapted to be refastenably attached to said receiving material; and
   a disposable assembly comprising a liquid pervious topsheet, a liquid impervious backsheet joined to said topsheet, an absorbent core intermediate said topsheet and said backsheet, and two outwardly facing patches of complementary hook type material on said backsheet, one said patch being in the front portion of said garment and one said patch being in the rear portion of said garment, said patches being adapted to be refastenably attached to said receiving material of said belt, said belt and said disposable assembly being detachable from each other.

2. A disposable absorbent garment according to claim 1 wherein said patches are joined to said backsheet in an arrangement selected from the group consisting of a generally longitudinal orientation, a generally lateral orientation and a patch in each quadrant of the backsheet.

3. A garment having a front portion, a rear portion and a longitudinal centerline, said garment comprising:
   a belt having a first face and a second face opposed thereto, said belt comprising receiving material and at least one patch of complementary hook type material adapted to be refastenably attached to said receiving material; and
   a disposable assembly comprising a liquid pervious topsheet, a liquid impervious backsheet joined to said topsheet, an absorbent core intermediate said topsheet and said backsheet, two longitudinally oriented flaps overlaying said topsheet, and an outwardly facing patch of complementary hook type material disposed on each of said flaps and adapted to be refastenably attached to said receiving material of said belt, said belt and said disposable assembly being detachable from each other.

4. A garment according to claim 3 wherein said topsheet and said backsheet are generally coextensive and said garment has longitudinal side margins laterally outboard of said core.

5. A garment according to claim 4 wherein said flaps are comprised of marginal portions of at least one of said backsheet and said topsheet.

6. A disposable absorbent garment according to claim 3 further comprising two patches of complementary hook type material on each said flap.

7. A disposable absorbent garment according to claim 6 wherein each said flap defines two corners, and each said patch of hook type material is juxtaposed with a said corner of said flap.

8. A disposable absorbent garment according to claim 7 wherein said patches have a longitudinal dimension and said belt has a width and said width of said belt is greater than said longitudinal dimension of a said patch.

9. A disposable absorbent garment according to claim 3 wherein said belt has at least one patch of said hook type material juxtaposed near an end of said belt.

10. A disposable absorbent garment according to claim 9 wherein said belt comprises receiving material substantially along the entire length of said belt intermediate said patches of complementary hook type material.

11. A disposable absorbent garment according to claim 3 further comprising indicia on said belt.

12. A disposable absorbent garment according to claim 11 wherein said indicia are longitudinally spaced apart.

13. A method of applying an absorbent garment to a wearer, said method comprising the steps of:
   providing a belt having a first face and a second face opposed thereto;
   providing a disposable assembly having a front waist margin and a rear waist margin;
   attaching said rear waist margin of said disposable assembly to the first face of said belt;
   encircling the waist of the wearer with said belt with the disposable assembly behind the wearer and downwardly oriented;
   attaching at least one end of said belt to any intermediate portion of said belt;
   drawing the disposable assembly between the legs of the wearer; and
   attaching the front waist margin of said disposable assembly to the second face of said belt.

14. A method of attaching an absorbent garment to a wearer in accordance with claim 13, wherein said belt has indicia, and further comprising the step of aligning said rear waist margin of said disposable assembly with said indicia.

15. A method of applying an absorbent garment to a wearer according to claim 14, wherein said disposable assembly has two flaps overlaying said core, and further comprising the step of inflecting said flaps of said disposable assembly prior to attaching said rear waist margin of said disposable assembly to said belt.

16. A garment having a front portion, a rear portion and a longitudinal centerline, said garment comprising:
   a belt having a first face and a second face opposed thereto;
   a disposable assembly comprising a liquid pervious topsheet, a liquid impervious backsheet joined to said topsheet, an absorbent core intermediate said topsheet and said backsheet; and
   at least two patches of adhesive joined to one of said belt and said disposable assembly, the other of said belt and said disposable assembly having a surface complementary to said adhesive patches, said adhesive and said complementary surface being adapted to permit attachment of said disposable assembly to said belt when said belt is encircled about the waist of a wearer, said belt and said disposable assembly being detachable from each other.

17. A garment according to claim 16 further comprising two longitudinally oriented flaps overlaying said topsheet.

18. A garment according to claim 17 wherein said patches of adhesive are disposed on said flaps.

* * * * *

UNITED STATES PATENT AND TRADEMARK OFFICE
CERTIFICATE OF CORRECTION

PATENT NO. : 4,964,860
DATED : October 23, 1990
INVENTOR(S) : William P. Gipson, Michael W. Mason and Thomas A. Hensler It is certified that error appears in the above-identified patent and that said Letters Patent is hereby corrected as shown below: Title page;

In reference to the filing date of the application "Jul.18, 1990" should be --Jul. 18, 1989--.

Column 1, line 3, "GARMENTc1 FIELD OF THE INVENTION" should be --GARMENT (centered) (return) FIELD OF THE INVENTION (centered)--.

Column 4, line 60, "lo allows" should be --allows--.
Column 5, line 10, before "or" insert --refers to a garment 10,--.

Column 7, line 50, "o without" should be --without--.

Column 9, line 20, "IV-0.55" should be --IV-.55--.

Signed and Sealed this

Tenth Day of November, 1992

Attest:

DOUGLAS B. COMER

Attesting Officer      Acting Commissioner of Patents and Trademarks

REEXAMINATION CERTIFICATE (2194th)
United States Patent [19]
Gipson et al.

[11] B1 4,964,860
[45] Certificate Issued Jan. 18, 1994

[54] DETACHABLE TWO PIECE ABSORBENT GARMENT

[75] Inventors: William P. Gipson; Michael W. Mason, both of Cincinnati; Thomas A. Hensler, West Chester, all of Ohio

[73] Assignee: The Procter & Gamble Company, Cincinnati, Ohio

Reexamination Request:
No. 90/002,547, Dec. 31, 1991

Reexamination Certificate for:
Patent No.: 4,964,860
Issued: Oct. 23, 1990
Appl. No.: 382,157
Filed: Jul. 18, 1989

Certificate of correction issued Nov. 10, 1992.

[51] Int. Cl.⁵ .................. A61F 13/00; A61F 13/15
[52] U.S. Cl. ............................. 604/391; 604/392
[58] Field of Search ............... 604/391, 392, 393, 396, 604/398, 332, 344, 345

[56] References Cited
U.S. PATENT DOCUMENTS

| | | | |
|---|---|---|---|
| 3,247,852 | 4/1966 | Schneider | 606/120 |
| 4,212,303 | 7/1980 | Nolan | 606/120 |

FOREIGN PATENT DOCUMENTS

| | | | |
|---|---|---|---|
| 2586558A1 | 3/1987 | France | |
| 2612770 | 9/1988 | France | 604/391 |
| WO88/07335 | 10/1988 | PCT Int'l Appl. | 604/391 |

*Primary Examiner*—Stephen C. Pellegrino

[57] ABSTRACT

A two piece garment for collecting bodily discharges is disclosed. The garment has a belt and a disposable assembly which are detachable and reattachable. The belt is intended to be reused, while the disposable assembly is intended to be discarded when soiled. The two components are attached to one another by hook and loop type fastening material, providing for adjustment to fit a wide range of wearer sizes.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–12, 14, 15 and 17–18 is confirmed.

Claims 13, 16 are cancelled.

Claim 1 is determined to be patentable as amended.

New claim 19 is added and determined to be patentable.

1. A garment having a front portion, a rear portion and a longitudinal centerline, said garment comprising:
a belt having a first face and a second face opposed thereto, said belt comprising receiving material and at least one patch of complementary hook type material adapted to be refastenably attached to said receiving material; and
a disposable assembly comprising a liquid pervious topsheet, a liquid impervious backsheet joined to said topsheet, an absorbent core intermediate said topsheet and said backsheet, two longitudinally oriented flaps overlaying said topsheet, *each said flap having a topsheet face oriented towards said topsheet and an opposed backsheet face* and an outwardly facing patch of complementary hook type material disposed on *said backsheet face of* each of said flaps and adapted to be refastenably attached to said receiving material of said belt, said belt and said disposable assembly being detachable from each other.

*19. A garment according to claim 3 wherein said belt is longitudinally adjustale relative to the disposable assembly.*

* * * * *